United States Patent [19]

Lee et al.

[11] Patent Number: 5,243,116

[45] Date of Patent: * Sep. 7, 1993

[54] ALKYLATION OF AROMATIC COMPOUNDS

[75] Inventors: Guo-shuh J. Lee; Juan M. Garces, both of Midland, Mich.; Garmt R. Meima; Matheus J. M. van der Aalst, both of Terneuzen, Netherlands

[73] Assignee: The Dow Chemical Company, Midland, Mich.

[*] Notice: The portion of the term of this patent subsequent to Mar. 30, 2010 has been disclaimed.

[21] Appl. No.: 325,177

[22] Filed: Dec. 22, 1989

Related U.S. Application Data

[63] Continuation-in-part of Ser. No. 323,530, Mar. 14, 1989, Pat. No. 5,004,841, which is a continuation-in-part of Ser. No. 123,741, Nov. 23, 1987, Pat. No. 4,891,448.

[51] Int. Cl.$^5$ .................. C07C 2/66; C07C 37/48; C07C 209/68

[52] U.S. Cl. .................. 585/467; 585/449; 585/452; 585/475; 564/409; 568/791; 568/794; 568/780; 568/781; 568/786; 568/782

[58] Field of Search ............. 568/628, 794, 791, 780, 568/781, 786, 782; 564/409; 585/449, 452, 475, 467

[56] References Cited

U.S. PATENT DOCUMENTS

| | | | |
|---|---|---|---|
| 3,140,253 | 7/1964 | Plank et al. | 208/120 |
| 3,251,897 | 5/1966 | Wise | 260/671 |
| 3,367,884 | 2/1968 | Reid, Jr. | 252/455 |
| 3,480,539 | 11/1969 | Voorhies, Jr. et al. | 208/111 |
| 3,485,748 | 12/1969 | Eberly et al. | |
| 3,551,510 | 12/1970 | Pollitzer et al. | 260/672 |
| 3,562,345 | 2/1971 | Mitsche | 260/672 |
| 3,597,155 | 8/1971 | Flanigen | 23/111 |
| 3,597,493 | 8/1971 | Frilette et al. | 260/666 |
| 3,631,120 | 12/1971 | Eberly, Jr. et al. | 260/671 |
| 3,641,177 | 2/1972 | Eberly, Jr. et al. | 260/671 C |
| 3,716,597 | 2/1973 | Mitsche et al. | 260/671 C |
| 3,719,026 | 3/1973 | Sand | |
| 3,763,260 | 10/1973 | Pollitzer | 260/672 T |
| 3,849,340 | 11/1974 | Pollitzer | 252/455 Z |
| 3,873,632 | 3/1975 | Pollitzer | 260/668 |
| 3,972,832 | 8/1976 | Butter et al. | 252/437 |
| 4,085,156 | 4/1978 | Frilette et al. | 260/671 R |
| 4,108,908 | 8/1978 | Rutledge | 568/730 |
| 4,151,120 | 8/1979 | Marcilly | |
| 4,169,111 | 9/1979 | Wight | 585/323 |
| 4,180,693 | 12/1979 | Marcilly | 585/475 |
| 4,182,692 | 1/1980 | Kiovsky et al. | 252/455 Z |
| 4,185,040 | 1/1980 | Ward et al. | 585/467 |
| 4,240,932 | 12/1980 | Alafandi et al. | 252/455 Z |
| 4,263,466 | 4/1981 | Colon et al. | 585/421 |
| 4,283,573 | 8/1981 | Young | 568/794 |

(List continued on next page.)

FOREIGN PATENT DOCUMENTS

| | | |
|---|---|---|
| 0202752 | 4/1986 | European Pat. Off. |
| 0285280 | 10/1988 | European Pat. Off. |
| 2084704 | 12/1971 | France |
| 56-133224 | 10/1981 | Japan |
| 56-156222 | 12/1981 | Japan |
| 58-159427 | 9/1983 | Japan |
| 122635 | 5/1988 | Japan |
| WO8803523 | 5/1988 | World Int. Prop. O. |

OTHER PUBLICATIONS

Kirk-Othmer *Encyclopedia of Chemical Technology*, 3rd Ed., vol. 14, John Wiley & Sons, New York, N.Y., pp. 395–427, 1981.

(List continued on next page.)

*Primary Examiner*—Marianne M. Cintins
*Assistant Examiner*—Margaret J. Page

[57] ABSTRACT

Alkylated benzenes such as ethylbenzene and cumene are produced by alkylation and/or transalkylation in the presence of an acidic mordenite zeolite catalyst having a silica/alumina molar ratio of at least 30:1 and a crystalline structure which is determined by X-ray diffraction to be a matrix of Cmcm symmetry having dispersed therein domains of Cmmm symmetry.

38 Claims, No Drawings

U.S. PATENTS DOCUMENTS

| | | | |
|---|---|---|---|
| 4,301,317 | 11/1981 | Young | 585/455 |
| 4,323,481 | 4/1982 | Kaduk | 252/455 Z |
| 4,361,713 | 11/1982 | Kaeding | 585/467 |
| 4,371,714 | 2/1983 | Young | 568/628 |
| 4,376,104 | 3/1983 | Ball et al. | 423/329 |
| 4,420,418 | 12/1983 | Chu | 502/77 |
| 4,447,669 | 5/1984 | Hamon et al. | 585/640 |
| 4,459,426 | 7/1984 | Inwood et al. | 585/323 |
| 4,480,142 | 10/1984 | Cobb | 585/465 |
| 4,525,466 | 6/1985 | Moretti et al. | 502/63 |
| 4,731,497 | 3/1988 | Grey | 585/455 |
| 4,745,095 | 5/1988 | Saito et al. | |
| 4,774,377 | 9/1988 | Barger et al. | 585/323 |
| 4,849,570 | 7/1989 | Bakas et al. | |

OTHER PUBLICATIONS

H. K. Beyer et al., *Studies in Surface Science and Catalysis*, vol. 18, pp. 133–140 (1984) M. Musa et al., *Zeolites*, vol. 7, pp. 427–433 (1987).

D. W. Breck, *Zeolite Molecular Sieves*, John Wiley & Sons, (1974) pp. 122–124 and 162–163.

J. D. Sherman and J. M. Bennett, "Framework Structures Related to the Zeolite Mordenite," *Molecular Sieves*, Advances in Chemistry Series, 121 (1973), pp. 52–65.

Chemical Abstracts 82:57148b (1975).

Chemical Abstracts 82:169681b (1975).

Derwent 84–141746/23 (1984).

Derwent 78145D/43 (1981).

Derwent 76464A/43 (1978).

Derwent 86–065632/10 (1986).

B. Sulikowski et al., *Polish Journal of Chemistry*, 60, 255–261 (1986).

I. M. Belen'Kaya et al. *Bulletin of the Academy of Sciences of USSR*, Division of Chemical Sciences 1971, #7, 1298–1303.

I. M. Belen'Kaya et al., *Bulletin of the Academy of Sciences of USSR*, Division of Chemical Sciences, 1971, #12, 2505–2509.

Derwent 84–026354/05 (1984).

K. A. Becker, H. G. Karge and W. D. Streubel, *Journal of Catalysis*, 28, 403–413 (1973).

ALKYLATION OF AROMATIC COMPOUNDS

CROSS-REFERENCE TO RELATED APPLICATIONS

This application is a continuation-in-part of co-pending application Ser. No. 323,530, filed Mar. 14, 1989 now U.S. Pat. No. 5,004,841, which is a continuation-in-part of application Ser. No. 123,741, filed Nov. 23, 1987 now U.S. Pat. No. 4,891,448.

BACKGROUND OF THE INVENTION

This invention relates to the use of mordenite zeolites as catalysts in the alkylation or transalkylation of aromatic compounds t produce cumene, ethylbenzene and other alkylated benzenes.

Cumene, also known as isopropylbenzene, is useful for the production of phenol, acetone and alphamethylstyrene. Ethylbenzene is useful in the production of styrene. Various processes for their manufacture are known.

Various processing schemes comprising alkylation and/or transalkylation reactions are known to produce monoalkylaromatic products such as cumene or ethylbenzene in high yields. However, existing processes are not without problems including the production of undesirable by-products. Examples of such by-products produced in conjunction with cumene include alkylating agent oligomers, heavy polyaromatic compounds and unwanted monoalkylated and dialkylated compounds such as n-propylbenzene, butylbenzenes and ethylbenzene. The production of unwanted xylenes are a particular problem in the production of ethylbenzene. Another problem with existing processes concerns the use of Friedel Crafts catalysts such as solid phosphoric acid or aluminum chloride. The phosphoric acid catalysts generally require the use of a water co-feed which produces a corrosive sludge by-product. Problems concerning the sludge by-product can be avoided by the use of zeolite catalysts.

It is known that aromatic hydrocarbons can be alkylated in the presence of acid-treated zeolite. U.S. Pat. No. 4,393,262 (1983) teaches that cumene is prepared by the alkylation of benzene with propylene in the presence of a specified zeolite catalyst. U.S. Pat. No. 3,140,253, (1964) and U.S. Pat. No. 3,367,884 (1968) broadly teach the use of acid-treated mordenite for the alkylation of aromatic compounds. However, such alkylations are generally not selective with respect to site and number of substitutions. Further, catalysts are often quickly deactivated requiring timely and costly replacements or reactivation.

Thus, there remains a need for an effective process for the preparation of alkylated benzenes having minimal levels of impurities utilizing a catalyst having low negative environmental impact and long life.

SUMMARY OF THE INVENTION

This invention is a process for alkylating benzene or substituted benzene to produce alkylated products having a low level of impurities. The invention is also directed to the transalkylation of polyalkylated aromatics or transalkylation of a mixture of diisopropylbenzene and benzene. The process comprises contacting the benzene with an alkylating agent having from about two to about eighteen carbon atoms in the presence of a catalyst under conditions such that alkylated benzene having a low content of impurities is produced. The catalyst exhibits long life and is simply reactivated by a hot benzene flush when necessary in the alkylation process. If required, reactivation may also be accomplished by a burn-off of carbonaceous deposits. The catalyst is an acidic mordenite zeolite having a silica/alumina molar ratio of at least 30:1. In addition, the mordenite zeolite catalyst has a crystalline structure which is determined by X-ray diffraction to be a matrix of Cmcm symmetry having dispersed therein domains of Cmmm symmetry.

Under the conditions of this process, cumene is produced having a surprisingly low bromine index and low levels of impurities such as n-propylbenzene, butylbenzene and ethylbenzenes. Ethylbenzene is produced having low levels of impurities such as xylenes. Surprisingly, the catalyst does not readily deactivate.

Cumene produced by the practice of this invention is useful in the production of phenol. Ethylbenzene produced is useful in the production of styrene.

DETAILED DESCRIPTION OF THE INVENTION

Any monocyclic aromatic compound may be alkylated or transalkylated by the process of this invention. The aromatic compound is preferably benzene or substituted benzene. Non-limiting examples of substituted benzenes which may be alkylated by the process of this invention include phenol and aniline. In the preparation of cumene and ethylbenzene, the aromatic compound is unsubstituted benzene or a mixture of benzene and dialkylated benzenes and other by-products produced in the alkylation of benzene with propylene or ethylene.

In a preferred embodiment, benzene is the aromatic compound which is alkylated using propylene as the alkylating agent to form cumene. In an alternative preferred embodiment, a mixture of benzene and diisopropylbenzene is transalkylated either in a separate reaction or concurrently with the propylene alkylation. The diisopropylbenzenes may be produced by the process of this invention or may be formed in a different alkylation process. In a third preferred embodiment, benzene is alkylated with ethylene to form ethylbenzene.

The aromatic compound may be used neat in a liquid state, or dissolved in a suitable solvent. Preferably, the aromatic compound is used in a neat liquid state. If a solvent is employed, any inert solvent which solubilizes the aromatic compound and does not hinder the alkylation reaction may be used. The preferred solvent is 1,3,5-triisopropylbenzene or decalin.

In the alkylation of benzene to form ethylbenzene, the preferred alkylation agent is ethylene. In the alkylation of benzene to produce cumene, the preferred alkylating agent is propylene. In another preferred embodiment wherein cumene is produced by transalkylation, it is preferred that a mixture of the m-, o- and p-isomers of diisopropylbenzene and benzene are transalkylated. The isomers may be formed as by-products in the alkylation of benzene with propylene to produce cumene either in the process of this invention or in a completely different process. When the alkylating agent is the mixture of isomers which ar formed as by-products in the alkylation of benzene with propylene to produce cumene, the cumene may be distilled off or otherwise removed from the by-product mixture. The mixture is then recycled to be transalkylated in the same reactor where benzene is alkylated with propylene. Alternatively, cumene is formed by some other alkylation process, such as a process using a solid phosphoric acid catalyst, and the by-products are used as the transalkylating agent with benzene is the process of this invention. Ethylbenzene may also by produced by transalkylation.

In a particularly preferred embodiment for the production of cumene, benzene is alkylated by the process of this invention using propylene as the alkylating agent. As discussed above, this process also produces diisopropylbenzene as a by-product. The diisopropylbenzene produced in the practice of this invention is a mixture of m-, o- and p-isomers enriched in the p-isomers. The cumene is separated from the by-products by techniques known in the art such as distillation. The remaining mixture including the diisopropylbenzene is recycled for transalkylation with benzene to form more cumene. The catalyst of this invention also shows reactant selectivity by transalkylating the para isomers at a greater rate than the ortho or meta isomers.

The catalyst useful in the practice of this invention is in acidic mordenite zeolite having a silica/alumina molar ratio of at least 30:1, a Symmetry Index (SI) as defined hereinafter of at least about 1.0, and a porosity such that the total pore volume is in the range from about 0.18 cc/g to about 0.45 cc/g, and the ratio of the combined meso- and macropore volume to the total pore volume is in the range from about 0.25 to about 0.75. For the purposes of this invention, a micropore has a radius in the range of about 3 angstrom units (Å) to 10 Å, a mesopore has a radius in the range of 10 Å to 100 Å, and a macropore has a radius in the range of 100 Å to 1000 Å.

The catalyst of the invention is an acid-modified zeolite with interconnecting twelve-ring and eight-ring channels. Zeolites have framework structures that are formally constructed from silicate and aluminate tetrahedra that share vertices. The tetrahedra may be linked to form pores or channels. The size of the pores is determined by the number of tetrahedra in the ring. Twelve-ring zeolites contain rings formed from twelve tetrahedra. Eight-ring zeolites contain rings formed from eight tetrahedra. The zeolites of this invention contain interconnecting twelve-ring and eight-ring channels. Examples of the zeolites suitable for use in this invention are mordenite, offretite and gmelinite. Mordenite-like zeolites, such as ECR-1 which is described in U.S. Pat. No. 4,657,748, and intergrowths of mordenite with other zeolites are also suitable catalysts; as are zeolites having a one-dimensional pore system with twelve-ring channels, such as type L or related zeolites. Preferably the catalyst is an acidic mordenite zeolite.

The catalyst useful in this invention is prepared by a process which comprises contacting with strong acid an acidic mordenite zeolite having a silica/alumina molar ratio less than 30:1 and a crystalline structure which is determined by X-ray diffraction to possess a Symmetry Index (SI) of from about 0.6 to about 1.0 under conditions sufficient to remove an amount of alumina sufficient to provide a silica/alumina molar ratio of at least 30:1.

Mordenite is an aluminosilicate whose typical unit cell contents are assigned the formula $Na_8[(AlO_2)_8(SiO_2)_{40}\cdot 24\ H_2O]$. Mordenite is the most siliceous natural zeolite with a silicon/aluminum mole ratio (Si/Al) of about 5/1. The dimensions of the twelve-ring pores are about $6.7 \times 7.0$ Å; the dimensions of the eight-ring pores are about $2.9 \times 5.7$ Å. The structure and properties of mordenite zeolite are described in *Zeolite Molecular Sieves*, by Donald W. Breck (John Wiley & Sons, 1974), at pages 122–124 and 162–163, which is incorporated herein by reference.

The catalyst of this invention is prepared from a mordenite zeolite typically containing cations of the alkali or alkaline earth metals, or alternatively ammonium ions. Preferably, the catalyst of the invention is prepared from a sodium mordenite zeolite; even more preferably, from a sodium mordenite zeolite having a Symmetry Index less than about 1.0. The Symmetry Index is a dimensionless number obtained from the X-ray diffraction pattern of the sodium mordenite being measured in the hydrated form. Standard techniques are employed to obtain the X-ray data. The radiation is the $K\alpha_1$ line of copper, and a Philips Electronics spectrometer is used. The mordenite zeolites exhibit an X-ray diffraction pattern whose diffraction peaks have d-spacings corresponding to those of crystalline mordenites as reported by J. D. Sherman and J. M. Bennett in "Framework Structures Related to the Zeolite Mordenite," *Molecular Sieves*; J. W. Meier and J. B. Uytterhoeven, eds., *Advances in Chemistry Series*, 121, 1973, pp. 52–65. The Symmetry Index is defined as the sum of the peak heights of the [111] (13.45, 2Θ) and [241] (23.17 2Θ) reflections divided by the peak height of the [350] (26.25 2Θ) reflection. Preferably, the Symmetry Index of the sodium mordenite ranges from about 0.50 to about 1.0. More preferably, the Symmetry Index of the sodium mordenite ranges from about 0.60 to about 1.0.

Four ordered crystalline structures have been proposed to describe the X-ray diffraction data available for natural and synthetic mordenite zeolites. (J. D. Sherman and J. M. Bennett, op. cit., p. 53) The symmetries of these four structures are Cmcm, Cmmm, Imcm, and Immm as these terms are defined by N. F. M. Henry and K. Lonsdale in *International Tables for X-ray Crystallography*, 3rd Ed., Volume 1, Kynoch Press (1969). X-ray diffraction data indicate that mordenites are either physical admixtures or intergrowths of the Cmmm, Imcm, or Immm structures with the Cmcm structure. Thus, mordenites can be generally described as having a crystalline structure comprising a matrix of Cmcm symmetry having dispersed therein domains of Cmmm, Imcm, or Immm symmetry, or mixtures thereof. Preferably, the mordenite of this invention has a crystalline structure comprising a matrix of Cmcm symmetry having dispersed therein domains of Cmmm symmetry. The Symmetry Index is related to the symmetries of the crystals present in the mordenite sample. A Symmetry Index in the range from about 0.60 to about 1.0 provides the optimum sodium mordenite as starting material for the process of this invention.

The crystallite size of the original sodium mordenite may be any size which yields a catalyst effective for the preparation of cumene having a low bromine index and low impurity levels. Typically, the crystallite size may be in the range from about 500 Å to about 5000 Å. Preferably, the crystallite size is in the range from about 500 Å to about 2000 Å; more preferably, from about 800 Å to about 1500 Å. Generally, the crystallites form aggregates which may be used as such or bound into larger particles for the process of this invention. For example, extrudate can be made for a packed-bed reactor by compressing the aggregates into binderless particles of suitable sizes. Alternatively, the extrudate can be made via use of binders well-known to those in the rat. The preferred particle size ranges from about 1 micron ($\mu$) to about 20$\mu$.

The original sodium mordenite zeolite described hereinabove, or its equivalent, is treated to obtain the catalyst of the invention for use in the alkylation process. The treatment involves contacting the mordenite with acid. In one preferred embodiment, the treatment involves contacting the mordenite with acid, calcining the acid-treated mordenite, and further contacting the calcined mordenite with strong acid. In an alternative preferred embodiment, the catalyst is prepared without being calcined.

The initial acid treatment serves to remove most of the sodium ions, or their equivalents, from the original mordenite. The treatment may remove a portion of the aluminum ions as well. Inorganic acids and organic acids are suitable compounds from which the hydrogen ions are obtained for the acid treatment. Examples of such acids are hydrochloric acid, hydrobromic acid, sulfuric acid, phosphoric acid, nitric acid, acetic acid, oxalic acid, and the like. Inorganic acids are the preferred source of hydrogen ions; with hydrochloric, nitric and phosphoric acids being more preferred and hydrochloric acid being most preferred. An equally acceptable initial treatment involves ion exchange with ammonium salts, such as ammonium chloride. By this method the sodium ions, or their equivalents, are removed, but the aluminum ions are not displaced. On heating the ammonium exchanged mordenite, ammonia is given off and the mordenite is converted to the acid form.

Typically, in the initial acid treatment the original sodium mordenite is slurried with an aqueous solution of the acid. The acid solution may have any concentration, providing the catalyst obtained possesses the properties and activity of the catalyst of this invention, these being described hereinafter. Preferably, the concentration of the aqueous acid solution is in the range from about 0.01 N to about 6N; more preferably in the range from about 0.5N to about 3.0N. The relative quantities of aqueous acid solution to mordenite solid which are employed may vary. Typically, the ratio is less than about 15 cc acid solution per gram mordenite solid. Preferably, the ratio is in the range from about 5 cc acid solution per gram mordenite solid to about 10 cc acid solution per gram mordenite solid. The temperature and the duration of the contact of the mordenite with the acid solution may also vary. Preferably, the mordenite is contacted with the acid at a temperature in the range from about 10° C. to about 100° C. Generally, the contact time between the acid solution and the mordenite may vary from about 5 minutes to about several hours. It is important that there be sufficient time for the acid solution to contact all of the mordenite particles. Preferably, the contact time is from about 5 minutes to about 60 minutes. The acid extraction, as described herein, may be repeated if desired. Afterwards, the mordenite is washed in water one or more times in order to rinse away soluble species from the mordenite. Preferably, the water wash is carried out at ambient temperature. Optionally, subsequent to the water wash the mordenite is dried in air at a temperature in the range from about 20° C. to about 150° C.

In one treatment, following the exchange with acid and drying in air, the acidic mordenite zeolite is calcined in air or heated in an inert atmosphere, such as nitrogen. It is believed that this heat treatment dislocated a portion of the aluminum from the zeolite framework; however, such a theory should not be taken as limiting of the scope of the invention. Typically, the temperature of the calcination or heating may range from about 250° C. to about 950° C. Preferably, the temperature of the calcination or heating is in the range from about 300° C. to about 800° C. More preferably, the temperature is in the range from about 400° C. to about 750° C. Most preferably, the temperature is from about 500° C. to about 700° C.

After calcining the acid-treated mordenite described hereinabove, the mordenite is subjected to an additional acid treatment for the purpose of further dealumination. The second acid treatment comprises contacting the calcined mordenite with a strong acid under conditions sufficient to produce the acidic mordenite catalyst of this invention. For the purposes of this invention a "strong" acid is defined as an acid which reacts essentially completely with the solvent to give the conjugate acid of the solvent. For example, if gaseous hydrogen chloride is dissolved in water, the acid-base reaction is complete to give the conjugate acid $H_3O+$ and $Cl-$. Preferably, the strong acid is an inorganic acid. More preferably, the strong acid is nitric acid, hydrochloric acid, or sulfuric acid. Most preferably, the strong acid is nitric acid. The concentration of the strong acid will vary depending on the acid selected. In general, the acid is employed in an aqueous solution of any concentration which provides for the extraction of aluminum from the calcined acidic mordenite, as described hereinafter. With nitric acid, for example, the concentration of the acid in the aqueous solution is preferably in the range from about 2N to about 15N. More preferably, the concentration of the acid is in the range from about 4N to about 12N. Most preferably, the concentration of the acid is in the range from about 6N to about 8N. The aqueous acid solution and the calcined mordenite are contacted in any ratio that provides the catalyst of the invention. Preferably, the ratio of aqueous acid solution to mordenite is in the range from about 3 cc acid solution per gram mordenite to about 10 cc acid solution per gram mordenite. More preferably, the ratio is about 5 cc acid solution per gram mordenite. The temperature and the duration of the contact may vary depending on the acid selected. Preferably, the mordenite is contacted with the acid solution at a temperature in the range from about ambient temperature taken as 22° C. to about 220° C. More preferably, the mordenite and the acid are contacted at a temperature which allows for boiling of the aqueous acid under atmospheric conditions. Preferably, the duration of the contact is from about 1 hour to about 6 hours; more preferably, from about 1 hour to about 3 hours; most preferably, for about 2 hours. When the contacting with strong acid is complete, the mordenite is filtered and washed repeatedly with water until the washings are acid-free. Preferably, the washed mordenite is heat treated and contacted with strong acid more than once. Lastly, the washed acidic mordenite zeolite is dried for several hours at a temperature in the range from about 100° C. to about 150° C. to remove physically adsorbed water. The dried acidic mordenite is activated by heating for about 2 hours at a temperature in the range from about 300° C. to about 700° C. This activation may drive off more strongly bound water and any residual adsorbates.

In an alternative embodiment, the original sodium mordenite is treated with acid and retreated with strong acid without the intermediate calcination step.

the catalysts useful in the process of this invention may also comprise a binder. Binders known to be useful with mordenite zeolite catalysts are useful for this purpose. Non-limiting examples of binders include alumina and silica with silica being preferred.

After the original sodium mordenite is treated with acid, optionally calcined, and retreated with strong acid according to the process of this invention, an acidic mordenite catalyst is obtained which is capable of converting benzene in a high conversion to cumene having a low bromine index and low levels of impurities or to ethylbenzene having a low level of impurities. This catalyst exhibits special characteristics by which it may be identified, specifically, the silica/alumina molar ratio, and the Symmetry Index and porosity as defined hereinafter.

An additional characteristic of the catalyst is its minimal deactivation in the alkylation of benzene or substituted benzenes. In the process of the present invention, the catalyst remains active for long periods of use. By remaining active, it is meant that the catalyst retains at least about 60, more preferably about 75 and most preferably about 90 percent of its activity for a period of at least about 500 hours of use, more preferably for at least about 750 hours of use and most preferably for at least about 900 hours of use. The catalyst preferably remains active significantly longer than 900 hours of use.

In the alkylation reaction of the present invention, the catalyst, should it show any deactivation, may be regenerated by a benzene flush at a temperature of about 350° C.

As a result of the acid extractions, the silica/alumina molar ratio ($SiO_2/Al_2O_3$) of the acidic mordenite catalyst is increased over that of the original sodium mordenite. Specifically, the acid-treated mordenite catalyst has a silica/alumina molar ratio of at least 30:1. Preferably, the silica/alumina molar ratio ranges from about 40:1 to about 300:1.

As a further result of the acid extractions and, optionally, calcination, the Symmetry Index of the mordenite catalyst is increased over that of the original mordenite. The Symmetry Index is as defined hereinbefore. Since the Symmetry Index is derived from X-ray data, the Index is related to the proportions of Cmcm, and Cmmm, Imcm, or Immm symmetries present in the catalyst. The increase in the Symmetry Index is indicative of the enrichment of the catalyst in the Cmcm component. For alkylations, a Symmetry Index of at least about 1 results in catalysts showing minimal deactivation that are capable of achieving high yields of alkylated benzenes. Preferably, the Symmetry Index ranges from about 1 to about 2.

A third property of the acid mordenite catalyst, by which it is identified, is the porosity. All zeolites possess pores which form as a natural consequence of zeolite crystal growth. New pores or modifications of existing pores can occur on treating the zeolites, for example, with heat or acid as in the process of this invention. Typically, pores are classified into micropores, mesopores and macropores. For the purposes of this invention a micropore is defined as having a radius in the range from about 3 Angstrom units (3 Å) to 10 Å. Likewise, a mesopore is defined as having a radius in the range from 10 Å to 100 Å, while a macropore is defined as having a radius from 100 Å to 1000 Å. After calcination and strong acid treatment, the acidic mordenite catalyst of this invention possesses micro-, meso- and macropores. The porosity of the catalyst may be distinguished by the total pore volume defined as the sum of the volumes of the micro-, meso-, and the macropores per gram catalyst. A catalyst of this invention has a total pore volume sufficient to provide a high yield of the desired alkylated benzene with low levels of impurities. Preferably, the total pore volume is in the range from bout 0.18 cc/g to about 0.45 cc/g. The porosity may be further distinguished by the relative distribution of meso- and macropores, as found in the ratio of the combined meso- and macropore volume to the total pre volume. A catalyst of this invention has a ratio of combined meso- and macropore volume to total pore volume sufficient to provide a high yield of the desired alkylated aromatics with low levels of impurities. Preferably, the ratio of the combined meso- and macropore volume to total pore volume is in the range from about 0.25 to about 0.75.

The measurement of the porosity, described hereinabove, is derived from surface area and pore volume measurements of mordenite powders obtained on any suitable instrument, such as a Quantachrome Digisorb-6 unit, using nitrogen as the adsorbate at the boiling point of nitrogen, 77 K. The total pore volume ($V_T$) is derived from the amount of nitrogen adsorbed at a relative pressure close to unity. It is accepted that this volume constitutes pores of less than 1000 Å in radius. As states earlier, for the purposes of this invention pores with radius of 10 Å or less are called micropores. Pores with radius from 10 Å to 100 Å are called mesopores, and pores with radius from 100 Å to 1000 Å are called macropores. Pores with radius in the 10 Å to 1000 Å range are known in the literature as "transitional pores." The micropore volume ($V_m$) in the presence of "transitional pores" is obtained by the t-method. The difference between the total pore volume and the micropore volume is the transitional pore volume, ($V_t = V_T - V_m$). The cumulative pore distribution in the transitional pore range is used to calculate the relative volume contributions of mesopores and macropores. For example, the mesopore volume is calculated by multiplying the transitional pore volume by the fraction of the cumulative pore volume from 120 Å to 100 Å, ($V_{me} = V_t f_{me}$). The macropore volume is then simply obtained by subtracting the mesopore volume from the transitional volume, ($V_{ma} = t_t - V_{me}$). This approach ensures that the equation $V_T = V_m + V_{me} + V_{ma}$ is satisfied. The adsorption isotherms obtained for the mordenite catalysts of this invention are of Type I, which are described by the Langmuir equation. The Langmuir surface area is obtained from such equation. The methods used to obtain surface areas and pore volumes are described by S. Lowell in *Introduction to Powder Surface Area* (John Wiley and Sons, 1979), or in the manuals provided with the Digisorb-6 instrument made by the Quantachrome Corporation.

The acidic mordenite catalyst, identified hereinabove, is capable of adsorbing biphenyl into the intracrystalline pore system, and conversely desorbing biphenyl. Biphenyl adsorption is effected by exposing the acidic mordenite to biphenyl vapors at 100° C. for a time sufficient to obtain near constant weight. Preferably, the adsorption capacity of the acidic mordenite for biphenyl is about 5 weight percent. More preferably, the capacity is about 10 weight percent. Biphenyl desorption is effected by heating the mordenite-biphenyl sample in a dynamic helium atmosphere from 25° C. to about 1000° C. at a heating rate of about 10° C./minute. The desorption of biphenyl may be followed experimentally by thermal gravimetric analysis combined with gas phase chromatography and mass spectrometry (TGA-GC-MS). It is found that weakly adsorbed biphenyl produces a weight loss at temperatures below about 300° C.; whereas, strongly adsorbed biphenyl produces a weight loss at temperatures from about 300° C. to as high as 1000° C. The amount of strongly adsorbed biphenyl is estimated by subtracting the amount of weakly adsorbed biphenyl from the total amount of biphenyl desorbed from the sample. A fully treated mordenite catalyst of this invention exhibits a sharp weight loss at temperatures below about 300° C. and little or no weight loss from 300° C. to 1000° C. In contrast, acid-exchanged mordenite exhibits a sharp weight loss at temperatures below about 300° C., and a second weight loss starting at about 300° C. and extending to 1000° C. It is believed that the weakly adsorbed biphenyl is located in sites from which there is relatively easy exit; whereas the strongly adsorbed biphenyl is located in sites from which there is relatively difficult exit. Thus, the acidic mordenite catalyst of this invention provides easy access and egress to adsorbed biphenyl. Such a theory, however, should not be construed to be binding or limiting of the scope of the invention.

The ratio of the benzene or substituted benzene to catalyst may be any weight ratio which produces the desired alkylated benzene with a relatively high selectivity and a low level of impurities. Preferred ratios will also be dependent on the reactor configuration. For example, in batch reactors, the weight ratio of benzene or substituted benzene to catalyst is preferably in the range from about 0.1:1 to about 2000:1. More preferably, the weight ratio is in the range from about 10:1 to about 500:1. Most preferably, the ratio is in the range from about 50:1 to about 100:1. Below the preferred lower limit of 0.1:1, the productivity will be very low. Above the preferred upper limit of 2000:1, the conversion of the aromatic compound may be low.

The ratio of benzene or substituted benzene to alkylating agent may vary depending on the identity of the alkylating agent, type of reaction such as batch or continuous and reaction conditions such as temperature, pressure and weight hourly space velocity (WHSV). When the alkylating agent is propylene, the ratio of benzene to propylene is preferably from about 10:1 to about 3:1 in a continuous reactor. The preferred ratio may be lower in a batch reactor with the propylene being supplied on demand. When diisopropylbenzene is used in a transalkylation reaction, the ratio of benzene to diisopropylbenzene is also preferably from about 10:1 to about 3:1. When alkylation and transalkylation reactions are taking place concurrently, the ratios of benzene to propylene and diisopropylbenzene are about 10:1. Similarly, when the alkylating agent is ethylene, the ratio of benzene to ethylene is preferably from about 10:1 to about 3:1 in a continuous reactor. As is recognized by one skilled in the art, when different reactor configurations are used, different ratios of reactants may be preferred.

The alkylating agent may be introduced to the reaction all at once, as in the case of a liquid alkylating reagent. Alternatively, the alkylating agent may be introduced to the reaction on demand until the desired degree of conversion is achieved, as in the case of a gaseous alkylating agent which is continuously fed into the reactor. When the alkylating/transalkylating agents are a mixture such as a mixture including both propylene and diisopropylbenzene, the components may be added independently.

The contacting of the benzene of substituted benzene with the alkylating agent in the presence of the catalyst may occur in a reactor of any configuration. Batch-type and continuous reactors, such as fixed bed, slurry bed, fluidized bed, catalytic distillation, or countercurrent reactors, are suitable configurations for the contact. Preferably, the reactor is fit with a means for observing and controlling the temperature of the reaction, a means for observing and measuring the pressure of the reaction, and optionally a means for agitating the reactants. The benzene or substituted benzene may be in the molten, liquid form or in solution. The alkylating agent may be introduced in the liquid or gaseous state, and may be added all at once at the start of the reaction, or fed continuously on demand from the reaction. The catalyst may be used in various forms, such as a fixed bed, moving bed, fluidized bed, in suspension in the liquid reaction mixture, or in a reactive distillation column.

The contacting of the reactants in the presence of the catalyst may occur at any temperature or pressure which will produce alkylated products having a low impurity content. In the production of cumene, the temperature is preferably in the range from about 100° C. to about 250° C., more preferably about 130° C. to 200° C. In the production of ethylbenzene, the temperature is preferably in the range from about 100° C. to about 250° C., more preferably about 180° C. to 250° C., the preferred lower limit of 100° C. the reaction proceeds slowly. Above the preferred upper limit of 250° C., the impurity level increases.

The pressure in the reactor in batch reactions is preferably in the range from about 10 psig to about 200 psig. More preferably, the pressure is in the range from about 10 psig to about 100 psig. Below the preferred lower limit of 10 psig, the alkylation rate is very low. Above the preferred upper limit of 200 psig the preferred propylene alkylating agent will polymerize severely. Other reactor configurations will have other preferred conditions.

The benzene, alkylating agent and/or transalkylating agent and catalyst are contacted for a time sufficient to convert the benzene to alkylated products, and sufficient to produce the desired yield of cumene. Generally, the contact time will depend on other reaction conditions, such as temperature, pressure and reagent-/catalyst ratios. In the production of cumene in a typical stirred batch reactor with a benzene: catalyst ratio of about 50:1, at 150° C., a propylene pressure of about 100 psig and a stirring rate of 2000 rpm, for example, the reaction time is preferably in the range from about 0.1 hour to about 10 hours. More preferably, the reaction time is in the range from about 1 hour to about 4 hours.

Following the alkylation/transalkylation of the benzene or substituted benzene, the product mixture may be separated by standard techniques.

For the purposes of this invention, the term "conversion" refers to the mole percent of benzene or substituted benzene which reacts to form alkylated products. Typically, in the batch reaction to produce cumene from benzene and propylene, the conversion achieved in the practice of this invention is in the range of about 10 to about 40 mole percent. Below the 10 percent conversion, the cumene recovery is not practical due to the large benzene recycle. Above 40 percent conversion, the amount of by-products such as diisopropylbenzene is large resulting in the need for a large transalkylation step.

Likewise, the term "benzene selectivity" refers to the mole percent of reacted benzene which is converted to desired product such as cumene or ethylbenzene.

Smaller amounts of various by-products such as the o-, p- and m-isomers of diisopropylbenzene and other alkylated benzenes such as n-propylbenzene, butylbenzenes and xylenes are also formed. Typically, the benzene selectivity to cumene or ethylbenzene ranges from about 70 mole percent to about 95 mole percent.

Another measure of selectivity is the "propylene selectivity" or "ethylene selectivity" which refers to the mole percent of propylene or ethylene which is converted to cumene or ethylbenzene respectively. Preferably, the propylene selectivity or ethylene selectivity is at least about 55 mole percent up to about 90 mole percent.

The concept of simultaneous high conversion and high selectivity to desired product may be expressed conveniently in terms of yield. For the purposes of the present invention, the term "yield" refers to the numerical product of conversion and selectivity. For example, a process to produce cumene according to the present invention operating at a benzene conversion of 15 percent, and a selectivity to cumene to 85 percent, would have a yield of cumene of 12.75 percent, which is the numerical product of 15 percent and 85 percent. Typically, the yield of cumene or ethylbenzene achieved in the process of this invention, not considering any recycle or reactants, is at least about 10 mole percent and is preferably at least about 15 mole percent.

An additional factor that is important is the presence of various impurities in the product. Even very small amounts certain impurities such as n-propylbenzene or propylene oligomers in the case of cumene, or xylenes in the case of ethylbenzene, create significant problems in various application. Processes run under different conditions result in different levels of impurities. Thus, a particular advantage of the process of the present invention is the low impurity levels. In the case of cumene production, low levels of oligomers as indicated by low bromine index is also important. In cumene production, the bromine index is preferably no greater than about 100, more preferably no greater than about 50 and most preferably no grater than about 20. Cumene produced by the process of this invention preferably contains less than about 1000 parts per million (ppm) impurities, more preferably less than about 200 ppm. Ethylbenzene produced by the process of this invention preferably has less than about 1000 ppm xylene impurities, more preferably less than about 500 ppm.

An additional characteristic of the cumene produced by the process of this invention is the amount of color in the product. The cumene produced by the practice of this invention is essentially colorless.

SPECIFIC EMBODIMENTS

The following examples are given to illustrate the catalyst and the process of this invention and should not be construed as limiting its scope. All percentages in the examples are mole percent unless otherwise indicated.

EXAMPLE 1—CATALYST PREPARATION

Catalyst C-1, not an embodiment of the invention, is an H-mordenite with a Symmetry Index of 0.88 with a $SiO_2/Al_2O_3$ ratio of 15.2 and 20 weight percent of a silica binder is used without further treatment. This is typical of commercially available mordenite. Its characteristics are given in Table I below.

Catalyst E-1, with a Symmetry Index of 2.1, is selected from commercially available hydrogen mordenites and used without further treatment and has the characteristics listed in Table I below. It also comprises 20 weight percent silica binder.

Catalyst E-2 is prepared by slurrying 300 g of Na-mordenite with a $SiO_2/Al_2O_3$ ratio of 19 and a Symmetry Index of 1.26 with 3000 ml of a 1M HCl solution for 30 minutes at room temperature. The product is washed with three 2000 ml portions of water and dried at 150° C. overnight. The dry solid is stirred in 1500 ml of 6M $HNO_3$ and heated under reflux for two hours. The product is washed with two 2000 ml portions of water and dried at 150° C. in air overnight. The Symmetry Index is 1.68. The characteristics of the catalyst are also listed in Table I below.

Catalyst E-3 is prepared from Na-mordenite with a $SiO_2/Al_2O_3$ ratio of 15 and a Symmetry Index of 0.97 using the procedure described for E-3. The Symmetry Index is 1.38. The characteristics of the catalyst are also listed in Table I below.

Catalyst E-4 has a Symmetry Index of 1.85 and is selected from commercially available hydrogen mordenite and used without further treatment. It has the characteristics listed in Table I below. This catalyst also includes 20 weight percent of a silica binder.

TABLE I

| Catalyst | $SiO_2/Al_2O_3$ (Molar Ratio) | Si/Na (Atomic Ratio) | BET ($m^2/g$) | Micro Pore Volume (ml/g) | Meso-Pore Volume (ml/g) | Macro-pore Volume (ml/g) | Total Pore Volume (ml/g) |
|---|---|---|---|---|---|---|---|
| C-1 | 15.2 | 96 | 389 | 0.190 | 0.023 | 0.036 | 0.244 |
| E-1 | 38 | 466 | 489 | 0.180 | 0.080 | 0.034 | 0.294 |
| E-2 | 84 | 1490 | 378 | 0.159 | 0.038 | 0.032 | 0.229 |
| E-3 | 108 | 4200 | 418 | 0.173 | 0.083 | 0.062 | 0.318 |
| E-4 | 156 | 4868 | 389 | 0.160 | 0.139 | 0.324 | 0.624 |

Catalysts C-1 and E-4 are extrudates with a diameter of about 1.5 mm. Catalysts E-1, E-2 and E-3 are crushed filtered particles of about 4 to 5 mm. Catalysts E-1 through E-4 are determined by X-ray diffraction to have Cmcm symmetry having dispersed therein domains of Cmmm symmetry.

TRANSALKYLATION TO PRODUCE CUMENE

Reactant feed is a mixture of distilled heavies from a cumene production and recycled benzene. The feed contains about 61 weight percent benzene; about 9 weight percent p-diisopropylbenzene (DIPB); about 8 weight percent m-DIPB; about 6 weight percent cumene; about 4 weight percent o-DIPB; about 3 percent 2-methyl, 2-phenylpentane; about 1 weight percent 3-methyl, 3-phenylpentane and about 8 weight percent various other impurities.

The pressure is 36 bar and the WHSV (feed weight hourly space velocity) is varied between about 0.4 and 0.8 $hr^{-1}$. Reactor effluent is cooled to room temperature prior to analysis which is performed on line by gas chromatography.

EXAMPLE 2—Transalkylation Using Catalyst E-3

In this experiment, the molar ratio of benzene to diisopropylbenzene is 5.9 and the WHSV is either 0.46 hr$^{-1}$ or 0.72 hr$^{-1}$ as shown in the tables below. The temperature is varied and conversion and selectivity are measured at 140° C., 150° C. and 155° C. These results are shown in Table II below.

TABLE II

| (CATALYST E-3) | | | | |
|---|---|---|---|---|
| Temperature (°C.) | 150 | 150 | 140 | 175 |
| Conversion (%) | | | | |
| m-DIPB | 59 | 70 | 27 | 75 |
| o-DIPB | 27 | 40 | 16 | 88 |
| p-DIPB | 82 | 86 | 68 | 88 |
| Total | 62 | 70 | 42 | 83 |
| Selectivity (%) | | | | |
| DIPB | 92 | 91 | 92 | 87 |
| Benzene | 102 | 105 | 102 | 114 |
| WHSV (hr$^{-1}$) | 0.72 | 0.46 | 0.46 | 0.46 |
| Time (hrs) | 90 | 60 | 170 | 100 |

The data in Table II demonstrates the long life of the catalyst used in the process of the present invention. No deactivation is observed when the reaction is run for the cumulative time indicated under the conditions shown.

The amount of specified by-products and of cumene in the feed and effluent are measured. These measured are done at a WHSV of 0.46 hr$^{-1}$. The results are shown in Table III below.

TABLE III

| | (CATALYST E-3) | | | |
|---|---|---|---|---|
| | Reactor Feed | Reactor Effluent at | | |
| | | 140° C. | 150° C. | 175° C. |
| Ethylbenzene (ppm) | 170 | 50 | 80 | 646 |
| n-propylbenzene (ppm) | — | 90 | 300 | 4722 |
| t-butylbenzene (ppm) | -135 | 915 | 820 | 825 |
| Cumene (wt %) | 4 | 17 | 25 | 28 |

The data above indicates that impurity production increases significantly at higher temperatures.

Using the conditions described above, the transalkylation reaction using Catalyst E-3 is run for a total of about 900 hours. No deactivation is shown over this time period.

EXAMPLE 3—TRANSALKYLATION USING CATALYST E-2

In this experiment, the molar ratio of benzene to diisopropylbenzene is 5.9 and the WHSV is 0.72 hr$^{-1}$. The temperature is varied and conversion and selectivity are measured at 140° C., 150° C. and 160° C. These results are shown in Table IV below.

TABLE IV

| (CATALYST E-2) | | | |
|---|---|---|---|
| Temperature (°C.) | 140 | 150① | 160 |
| Conversion (%) | | | |
| m-DIPB | −5 | 33 26 | 63 |
| o-DIPB | 11 | 22 18 | 36 |
| p-DIPB | 54 | 70 68 | 84 |
| Total | 23 | 46 42 | 66 |
| Selectivity (%) | | | |
| DIPB | 95 | 95 95 | 93 |
| Benzene | 85 | 98 98 | 97 |
| Time (hrs) | 120 | — 210 | 175 |

①Slight deactivation is observed at this temperature. The first column represents results at the beginning of the reaction at this temperature and the second column indicates results after 210 hours.

The data in Table IV demonstrates the long life of this catalyst used in the process of the present invention. Slight deactivation is shown at 150° C. In this situation, the conversion of DIPB drops from 46 to 42 percent. AT 140° C. and 160° C., no deactivation is observed.

The amount of specified by-products and of cumene in the feed and effluent are measured. These measurements are done at a WHSV at 0.46 hr$^{-1}$. The results are shown in Table V below.

TABLE V

| | (CATALYST E-2) | | |
|---|---|---|---|
| | Reactor Feed | Reactor Effluent at | |
| | | 150° C. | 160° C. |
| Ethylbenzene (ppm) | 20 | 50 | 100 |
| n-propylbenzene (ppm) | <10 | 150 | 560 |
| t-butylbenzene (ppm) | 130 | 840 | 790 |
| s-butylbenzene (ppm) | 40 | 190 | 370 |
| Cumene (wt %) | 4.6 | 18.0 | 24.5 |

EXAMPLE 4—TRANSALKYLATION USING CATALYSTS E-1 and E-4

In this experiment, the molar ratio of benzene to diisopropylbenzene is 5.8 and the WHSV is either 0.45 hr$^{-1}$ or 0.74 hr$^{-1}$. The temperature is varied and conversion and selectivity are measured at 150° C. and 175° C. These results are shown in Table VI below.

TABLE VI

| (CATALYSTS E-4 AND E-1) | | | | | |
|---|---|---|---|---|---|
| Temperature (°C.) | 150 | 150 | 150 | 150 | 175 |
| Catalyst | E-4 | E-4 | E-1 | E-1 | E-4 |
| Conversion (%) | | | | | |
| m-DIPB | <1 | 18 | 73 | 73 | 71 |
| o-DIPB | 5 | 14 | 43 | 69 | 66 |
| p-DIPB | 58 | 65 | 87 | 87 | 86 |
| Total | 25 | 37 | 73 | 78 | 76 |
| Selectivity (%) | | | | | |
| DIPB | 96 | 94 | 93 | 92 | 91 |
| Benzene | 95 | 99 | 110 | 120 | 110 |
| WHSV (hr$^{-1}$) | 0.74 | 0.45 | 0.75 | 0.45 | 0.74 |
| Time (hrs) | 70 | 110 | 70 | 70 | 110 |

The data in Table VI demonstrates the long life of the catalysts used in the process of the present invention.

The amount of specified by-products and of cumene in the feed and effluent are measured. These measurements are done at a WHSV of 0.46 hr$^{-1}$. The results are shown in Table VII below.

TABLE VII

| | (CATALYSTS E-4 AND E-1) | | | | |
|---|---|---|---|---|---|
| | Reactor Feed | Reactor Effluent at | | | |
| | | 150° C. | 150° C. | 175° C. | 150° C. | 150° C. |
| Catalyst | — | E-4 | E-4 | E-4 | E-1 | E-1 |
| Ethylbenzene (ppm) | <10 | <10 | 90 | 150 | 140 | 230 |
| n-propyl- | <10 | 10 | 120 | 510 | 700 | 1210 |

TABLE VII-continued

| (CATALYSTS E-4 AND E-1) | | | | | |
|---|---|---|---|---|---|
| Reactor Feed | Reactor Effluent at | | | | |
| | 150° C. | 150° C. | 175° C. | 150° C. | 150° C. |
| benzene (ppm) | | | | | |
| t-butyl-benzene (ppm) | 200 | 1020 | 990 | 870 | 640 | 620 |
| s-butyl-benzene (ppm) | <10 | 100 | 140 | 500 | 410 | 560 |
| WHSV (hr$^{-1}$) | — | 0.74 | 0.45 | 0.74 | 0.75 | 0.45 |
| Cumene (wt %) | 5.8 | 13.8 | 17.5 | 28.7 | 28.0 | 29.1 |

EXAMPLE 5—BROMINE INDEX IN TRANSALKYLATION PRODUCT

Using Catalysts E-1 and E-4 and the procedure described above for the transalkylation reaction, cumene is produced at the temperatures and WHSV shown in Table VIII. The bromine index of the cumene is measured sing ASTM D-1492-7B. Results obtained are shown in Table VIII below.

TABLE VIII

| Catalyst | Temperature (°C.) | WSHV (hr$^{-1}$) | Bromine Index (mg/100 g) |
|---|---|---|---|
| E-1 | 130 | 0.78 | 3 |
| | 140 | 0.74 | 5 |
| | 150 | 0.75 | 2 |
| | 150 | 0.46 | 3 |
| | 160 | 0.73 | 3 |
| E-4 | 150 | 0.76 | 2 |
| | 150 | 0.46 | 5 |
| | 175 | 0.75 | 12 |

COMPARATIVE EXAMPLE 1—TRANSALKYLATION USING CATALYST C-1 (NOT AN EMBODIMENT OF THE INVENTION)

Catalyst C-1 is tested using similar conditions and shows significant deactivation after 110 hours of use. The percentage conversion of DIPB drops from about 56 percent to about 15 percent in this time period. The levels of impurities produced at the highest activity are 320 ppm n-propylbenzene, 670 ppm t-butylbenzene and 290 ppm s-butylbenzene.

EXAMPLE 6—ALKYLATION OF BENZENE WITH PROPYLENE USING CATALYST E-4

A feed stream of benzene, propylene and propane is subjected to alkylation at various temperatures. The content of the feed stream is varied. Feed Stream 1 91.4 weight percent benzene, 8.5 weight percent propylene and 0.1 weight percent propane (5.8 molar ratio of benzene to propylene). Feed Stream 2 to 91.0 weight percent benzene, 8.9 weight percent propylene and 0.1 weight percent propane (5.5 molar ratio of benzene to propylene). Feed Stream 3 is 87.4 weight percent benzene, 12.4 weight percent propylene and 0.2 weight percent propane (3.8 molar ratio of benzene to propylene). Feed Stream 4 is 93.4 weight percent benzene, 6.5 weight percent propylene and 0.1 weight percent propane ()7.7 molar ratio of benzene to propylene). The results are presented in Table IX below.

TABLE IX

| (CATALYST E-4) | | | | | | | | |
|---|---|---|---|---|---|---|---|---|
| Temp. (°C.) | Benzene Selectivity (%) | Propylene Selectivity (%) | DIPB Selectivity (%) | m-DIPB Selectivity (%) | o-DIPB Selectivity (%) | p-DIPB Selectivity (%) | Time (Hr) | Reactant Feed Composition |
| 130 | 71.1 | 54.6 | 28.5 | 4.9 | — | 23.6 | 22 | 1 |
| 145 | 74.0 | 59.2 | 25.0 | 9.9 | — | 15.1 | 22 | 1 |
| 155 | 78.8 | 65.6 | 20.1 | 12.2 | — | 7.9 | 24 | 1 |
| 165 | 86.4 | 73.6 | 13.7 | 9.3 | — | 4.4 | 30 | 1 |
| 175 | 91.6 | 83.4 | 7.9 | 5.3 | — | 2.6 | 80 | 1 |
| 185 | 94.8 | 88.0 | 5.1 | 3.3 | — | 1.7 | 48 | 2 |
| 175 | 91.1 | 83.0 | 8.6 | 5.7 | — | 2.9 | 24 | 3 |
| 175 | 94.7 | 87.0 | 5.1 | 3.4 | — | 1.7 | 45 | 4 |

EXAMPLE 7—BROMINE INDEX IN ALKYLATION PRODUCT

Using Catalyst E-4 and the general process described in Example 6 above, the bromine index of the cumene produced at various temperatures and benzene/propylene ratios is measured using ASTM D-1492-7B. The results obtained are shown in Table X below.

TABLE X

| Temperature (°C.) | Benzene/Propylene Molar Ratio | Bromine Index (mg/100 g) |
|---|---|---|
| 145 | 5.8 | 2 |
| 155 | 5.8 | <4 |
| 165 | 5.8 | <1 |
| 175 | 5.8 | <1 |
| 185 | 5.5 | <1 |
| 175 | 3.8 | <1 |
| 175 | 7.7 | <1 |

EXAMPLE 8—ALKYLATION OF PHENOL

A 100-g portion of phenol, 50 g of 1-octene and 100 g of 1,3,5-triisopropylbenzene are reacted in the presence of a dealuminated mordenite catalyst having a silica/alumina ratio of about 156. The reactants are contacted at 200° C. for 2 hours at a starting pressure of 38 psig. The product formed is colorless p-octylphenol. As determined by gas chromatography, the conversion of phenol is 40 percent, the conversion of octene is 80 percent and the p-octylphenol formed is at least 98 percent pure.

EXAMPLE 9—PREPARATION OF ETHYLBENZENE

Using the general procedure described in Example 6, benzene is alkylated with ethylene to form ethylbenzene. The catalyst using has a $SiO_2/Al_2O_3$ ratio of 44, the BET is 403 m$^2$/g, the micropore volume is 0.137 ml/g, the mesopore volume is 0.070 ml/g, the macropore volume is 0.040 ml/g, the total pore volume is 0.237 ml/g and the Symmetry Index is 1.52. The ratio of ethylene to benzene is 0.41. The temperature is 220° C. and the pressure is 36 bar. The yield of ethylbenzene is 32.9 percent. The concentration of impurities are: toluene, 250 ppm; xylenes, 60 ppm; cumene, 220 ppm; n-propylbenzene, 150 ppm; ethyltoluene, 140 ppm; and butylbenzene, 200 ppm. No deactivation was observed after 140 hours of operation.

What is claimed is:

1. A process of alkylating benzene or substituted benzene, or transalkylating dialkylated benzene comprising contacting the benzene or substituted benzene with an alkylating agent having from two to eighteen carbon atoms in the presence of a catalyst, or contacting the dialkylated benzene with benzene in the presence of the catalyst, said catalyst consisting essentially of an acidic mordenite zeolite having a silica/alumina molar ratio of at least 30:1 and a crystalline structure which is determined by X-ray diffraction to be a matrix of Cmcm symmetry having dispersed therein domains of Cmmm symmetry and having a Symmetry Index of at least about 1, the catalyst being prepared by a method which comprises
(A) calcining an acidic mordenite having a Symmetry Index between about 0.50 and about 1.0 and having a silica/alumina molar ratio less than 30:1 in air or heating the acidic mordenite in an inert atmosphere at a temperature in the range from about 250° C. to about 950° C., and
(B) contacting the calcined or heated acidic mordenite with strong acid to form an acidic mordenite having a silica/alumina molar ratio of at least 30:1 and having a Symmetry Index of at least about 1, and optionally
(C) repeating Steps (A) and (B),
under reaction conditions such that an alkylated benzene or alkylated substituted benzene is produced and the catalyst retains at least about 60 percent of its activity for a period of at least about 500 hours of use.

2. The process of claim 1 wherein benzene is contacted with an alkylating agent having two to twelve carbon atoms to produce essentially colorless alkylated benzene.

3. The process of claim 2 wherein the alkylating agent is propylene.

4. The process of claim 2 wherein the alkylating agent is ethylene.

5. The process of claim 1 wherein the catalyst has a silica/alumina molar ratio of at least about 40:1 and no greater than about 300:1.

6. The process of claim 1 wherein the catalyst has a Symmetry Index of about 1 to about 2.

7. The process of claim 1 wherein a temperature in the range from about 100° C. to about 250° C. is maintained during the alkylation or transalkylation.

8. The process of claim 4 wherein a temperature in the range from about 200° C. to about 250° C. is maintained during the alkylation of transalkylation.

9. The process of claim 1 wherein the benzene or substituted benzene is in a neat, liquid state and the alkylating agent is dissolved in the liquid state.

10. The process of claim 1 wherein the benzene or substituted benzene is dissolved in a solvent.

11. The process of claim 1 wherein substituted benzene is alkylated.

12. The process of claim 11 wherein the substituted benzene is phenol.

13. The process of claim 11 wherein the substituted benzene is aniline.

14. The process of claim 1 wherein in Step A the temperature is in the range from about 300° C. to about 800° C., and wherein in Step B the strong acid is an inorganic acid in a second aqueous acid solution having a concentration in the range from about 4N to about 12N, the ratio of the second aqueous acid solution to acidic mordenite is in the range from about 3 cc second aqueous acid solution per gram acidic mordenite to about 10 cc second aqueous acid solution per gram acidic mordenite, the contacting occurring at a temperature in the range from about 22° C. to about 220° C.

15. A process of producing an alkylated benzene comprising cumene and ethylbenzene by transalkylation comprising contacting benzene and a mixture of dialkylated benzenes in the presence of a catalyst, said catalyst consisting essentially of an acidic mordenite zeolite having a silica/alumina molar ratio of at least 30:1 and a crystalline structure which is determined by X-ray diffraction to be a matrix of Cmcm symmetry having dispersed therein domains of Cmmm symmetry and having a Symmetry Index of at least about 1, the catalyst being prepared by a method which comprises
(A) calcining an acidic mordenite having a Symmetry Index between about 0.50 and about 1.0 and having a silica/alumina molar ratio less than 30:1 in air or heating the acidic mordenite in an inert atmosphere at a temperature in the range from about 250° C. to about 950° C., and
(B) contacting the calcined or heated acidic mordenite with strong acid to form an acidic mordenite having a silica/alumina molar ratio of at least 30:1 and having a Symmetry Index of at least about 1, and optionally
(C) repeating Steps (A) and (B),
under reaction conditions such that an essentially colorless alkylated benzene is produced and the catalyst retains at least about 60 percent of its activity for a period of at least about 500 hours of use.

16. The process of claim 15 wherein the catalyst has a silica/alumina molar ratio of at least about 40:1 and no greater than about 300:1.

17. The process of claim 15 wherein the catalyst has a Symmetry Index of about 1 to about 2.

18. The process of claim 15 wherein a temperature in the range from about 100° C. to about 250° C. is maintained during the alkylation of transalkylation.

19. The process of claim 4 wherein a temperature in the range from about 200° C. to about 250° C. is maintained during the alkylation or transalkylation.

20. The process of claim 15 wherein the aromatic compound is dissolved in a solvent.

21. The process of claim 15 wherein the dialkylated benzenes are produced by the alkylation of benzene with an alkylating agent selected from the group consisting of ethylene and propylene in a process using a catalyst comprising an acidic mordenite zeolite having a silica/alumina ratio of at least 30:1 and a crystalline structure which is determined by X-ray diffraction to be a matrix of Cmcm symmetry having dispersed therein domains of Cmmm symmetry.

22. The process of claim 15 wherein the mixture of dialkylated benzenes is a mixture of the o-, m- and p-isomers of diisopropylbenzene produced by the alkylation of benzene with propylene to produce cumene in a process using a solid phosphoric acid catalyst.

23. The process of claim 15 wherein the dialkylated benzenes are a mixture of the o-, m- and p-isomers of diisopropylbenzene and the para isomer of the diisopropylbenzene reacts at a greater rate than the ortho or meta isomer.

24. The process of claim 15 wherein in Step A the temperature is in the range from about 300° C. to about 800° C., and wherein in Step B the strong acid is an inorganic acid in a second aqueous acid solution having a concentration in the range from about 4N to about 12N, the ratio of the second aqueous acid solution to acidic mordenite is in the range from bout 3 cc second aqueous acid solution per gram acidic mordenite to about 10 cc second aqueous acid solution per gram acidic mordenite, the contacting occurring at a temperature in the range from about 22° C. to about 220° C.

25. A process of producing cumene by alkylation or transalkylation comprising contacting benzene with propylene or diisopropylbenzene in the presence of a catalyst, said catalyst consisting essentially of an acidic mordenite zeolite having a silica/alumina molar ratio of at least 30:1 and a crystalline structure which is determined by X-ray diffraction to be a matrix of Cmcm symmetry having dispersed therein domains of Cmmm symmetry and having a Symmetry Index of at least about 1, the catalyst being prepared by a method which comprises
(A) calcining an acidic mordenite having a Symmetry Index between about 0.50 and about 1.0 and having a silica/alumina molar ratio less than 30:1 in air or heating the acidic mordenite in an inert atmosphere at a temperature in the range from about 250° C. to about 950° C., and
(B) contacting the calcined or heated acidic mordenite with strong acid to from an acidic mordenite having a silica/alumina molar ratio of at least 30:1 and having a Symmetry Index of at least about 1,a nd optionally
(C) repeating Steps (A) and (B),
under reaction conditions such that essentially colorless cumene is produced and the catalyst retains at least about 60 percent of its activity for a period of at least about 500 hours of use.

26. The process of claim 25 wherein in Step A the temperature is in the range from about 300° C. to about 800° C., and wherein in Step B the strong acid is an inorganic acid in a second aqueous acid solution having a concentration in the range from about 4N to about 12N, the ratio of the second aqueous acid solution to acidic mordenite is in the range from about 3 cc second aqueous acid solution per gram acidic mordenite to about 10 cc second aqueous acid solution per gram acidic mordenite, the contacting occurring at a temperature in the range from about 22° C. to about 220° C.

27. The process of claim 25 wherein the catalyst has a silica/alumina molar ratio of at least about 40:1 and no greater than about 300:1.

28. The process of claim 25 wherein the catalyst has a Symmetry Index of about 1 to about 2.

29. The process of claim 25 wherein a temperature in the range from about 100° C. to about 250° C. is maintained during the alkylation or transalkylation.

30. The process of claim 25 wherein the benzene is in a neat, liquid state and the diisopropylbenzene or propylene is dissolved in the liquid state.

31. The process of claim 25 wherein the benzene is dissolved in a solvent.

32. A process of producing ethylbenzene by alkylation or transalkylation comprising contacting benzene with ethylene or diethylbenzene in the presence of a catalyst, said catalyst consisting essentially of an acidic mordenite zeolite having a silica/alumina molar ratio of at least 30:1 and a crystalline structure which is determined by X-ray diffraction to be a matrix of Cmcm symmetry having dispersed therein domains of Cmmm symmetry and having a Symmetry Index of at least about 1, the catalyst being prepared by a method which comprises
(A) calcining an acidic mordenite having a Symmetry Index between about 0.50 and about 1.0 and having a silica/alumina molar ratio less than 30:1 in the presence of an oxygen containing gas or heating the acidic mordenite in an inert atmosphere at a temperature in the range from about 250° C. to about 950° C., and
(B) contacting the calcined or heated acidic mordenite with strong acid to form an acidic mordenite having a silica/alumina molar ratio of at least 30:1 and having a Symmetry Index of at least about 1, and optionally
(C) repeating Steps (A) and (B),
under reaction conditions such that an essentially colorless ethylbenzene is produced and the catalyst retains at least about 60 percent of its activity or a period of at least about 500 hours of use.

33. The process of claim 32 wherein in Step A the temperature is in the range from about 300° C. to about 800° C. and wherein in Step B the strong acid is an inorganic acid in a second aqueous acid solution having a concentration in the range from about 4N to about 12N, the ratio of the second aqueous acid solution to acidic mordenite is in the range from about 3 cc second aqueous acid solution per gram acidic mordenite to about 10 cc second aqueous acid solution per gram acidic mordenite, the contacting occurring at a temperature in the range from about 22° C. to about 220° C.

34. The process of claim 32 wherein the catalyst has a silica/alumina molar ratio of at least about 40:1 and no greater than about 300:1.

35. The process of claim 32 wherein the catalyst has a Symmetry Index of about 1 to about 2.

36. The process of claim 32 wherein a temperature in the range from about 100° C. to about 250° C. is maintained during the alkylation or transalkylation.

37. The process of claim 32 wherein the benzene is in a neat, liquid state and the diethylbenzene or ethylene is dissolved in the liquid state.

38. The process of claim 32 wherein the benzene is dissolved in a solvent.

* * * * *